United States Patent [19]

Kliment

[11] Patent Number: 4,587,129

[45] Date of Patent: May 6, 1986

[54] HYDROPHILIC GELS CONTAINING HIGH AMOUNTS OF FRAGRANCE

[75] Inventor: Charles K. Kliment, Princeton, N.J.

[73] Assignee: National Patent Development Co., New York, N.Y.

[21] Appl. No.: 383,963

[22] Filed: Jun. 1, 1982

Related U.S. Application Data

[63] Continuation of Ser. No. 46,317, Mar. 7, 1979, abandoned.

[51] Int. Cl.$^4$ .................... A23L 2/26; A61K 7/46
[52] U.S. Cl. ................... 426/534; 252/522 A; 424/33; 424/76; 523/100; 523/102
[58] Field of Search ............. 252/522 A, 522 R, 316; 424/33, 76; 426/534

[56] References Cited

U.S. PATENT DOCUMENTS

| | | | |
|---|---|---|---|
| 3,220,960 | 11/1965 | Wichterle | 521/149 |
| 3,400,890 | 9/1968 | Gould | 252/522 A |
| 3,567,118 | 3/1971 | Shepherd et al. | 252/522 A |
| 3,574,826 | 4/1971 | Shepherd et al. | 424/33 |
| 3,576,760 | 4/1971 | Gould et al. | 424/76 |
| 3,577,512 | 5/1971 | Shepherd et al. | 424/33 |
| 3,577,516 | 5/1971 | Gould et al. | 424/33 |
| 3,596,833 | 9/1968 | Gould | 252/522 A |
| 3,681,248 | 8/1972 | Gould et al. | 252/522 A |
| 3,772,215 | 11/1973 | Gould et al. | 252/522 A |
| 3,868,447 | 2/1975 | Kliment | 252/522 A |
| 3,886,125 | 5/1975 | Chromecek | 424/76 |
| 3,966,902 | 6/1976 | Chromecek | 424/76 |
| 4,009,684 | 3/1977 | Kliment et al. | 424/76 |

*Primary Examiner*—Thomas A. Waltz
*Attorney, Agent, or Firm*—Cushman, Darby & Cushman

[57] ABSTRACT

A copolymer of at least one hydroxy (lower alkyl) 2-alkenoate, e.g., hydroxyethyl methacrylate, with 35 to 80%, preferably 50 to 80%, of at least one diester of an alkenedioic acid in hydrogel form is employed to entrap flavors and fragrances in an amount of 5 to 80% or even up to 90%, preferably 30 to 80% of the total formulation. A solvent can also be present in an amount up to 80%, preferably 10–80% of the total weight of the formulation.

6 Claims, No Drawings

HYDROPHILIC GELS CONTAINING HIGH AMOUNTS OF FRAGRANCE

This is a continuation of application Ser. No. 46,317 filed Mar. 7, 1979, and now abandoned.

BACKGROUND OF THE INVENTION

This invention relates to novel gels, particularly hydrogels, having flavors or fragrances entrapped therein.

Hydroxy (lower alkyl) acrylate and methacrylate polymers (some of which are available under the trademark HYDRON) are known to be excellent slow-release vehicles and this use is a subject of many patents and patent applications. Both the crosslinked and soluble polymers of this type have this property and have been shown to slowly release biologically active compounds, flavors, fragrances, etc. In all the published (and patented) uses the ratio of the active substance to polymer cannot be much higher than 1:1 and is usually less, normally being less than 30% in the case of flavors and fragrances, for example, because otherwise the cohesiveness of the polymeric matrix is lost and as a result of this it is impossible to obtain continuous films from the soluble polymer or definite, shape retaining objects from the crosslinked polymers. The amount of crosslinking agent is usually kept low, between 0.05 to 2.0 weight %. Only for some special uses higher amounts of the crosslinking agent were proposed, usually between 10 to 15 weight % U.S. Pat. Nos. 3,574,286, 3,618,231, and 3,761,286, the highest being 20 weight % in U.S. Pat. No. 3,470,883. Other patents of interest in this connection are U.S. Pat. Nos. 2,976,576; 3,699,089; 3,551,556; 3,689,634; 3,697,643; and U.S. Pat. No. Re. 27,401.

The use of more than 20% of crosslinking agent is shown in U.S. Pat. Nos. 3,503,942; 3,792,028; and 3,728,315. However, none of these latter patents are concerned with the use of polymers for loading fragrances and flavorings.

Prior art hydroxyalkyl acrylate and methacrylate polymers which have been loaded with fragrances and flavorings as indicated supra generally had low amounts of crosslinking agent and generally low fragrance loading (up to 30% and usually much less). These polymers were generally meant to be pulverized. High fragrance loading under these conditions is impractical, because if the mixture polymerizes at all, the gel is not self-supporting but mushy, crumbling or flowing. In water the product usually does not have any cohesion altogether.

Typical prior art disclosed polymeric products or articles made from, for example, HEMA (hydroxyethyl methacrylate), up to 5 weight % diester (based on the total weight of monomers), and up to 25 weight % of fragrances, essences, flavors, and the like ("FF" for cconvenience), based on the total weight of the formulation. Approximately 25 weight % of FF represents the highest loading in the formulation since as stated greater amounts result in a product or article which loses its, self-supporting or self-retaining properties. Thus, the prior art products were useful in the form of powders or coatings, etc., in which, for example, moisture activated the FF and thereby caused its slow release to the environment.

If one desired to manufacture a prior art product which would self-activate the slow release of the FF, one would incorporate into the polymerizable formulation a solvent, e.g., 20 weight % (based on the total weight of the formulation).

However, in the case such a solvent were added the resulting product is soft, crumbles under mild hand pressure, is not truly self-supporting, and is opaque whereas the commercial trade desires clear, hard, self-supporting, slow-release articles.

SUMMARY OF THE INVENTION

It has now been found that there can be prepared novel solid, normally self-supporting, shape-retaining gel articles which contain upwards to 90 weight % of flavors, essence, fragrances, perfume oils, and the like (hereinafter designated as "FF" for convenience), based on the total weight of the dry composition, e.g., 5 to 80 weight %, preferably 10 to 80 weight %, usually at least 30 weight % and even 50 to 80 or 90 weight % providing that the gel is made from a polymer of (1) at least one hydroxy (lower alkyl) 2-alkenoate or hydroxy (lower alkoxy) lower alkyl 2-alkenoate or hydroxy poly (lower alkoxy lower alkyl 2-alkenoate, and (2) at least one polyethylenically unsaturated crosslinking agent wherein the amount of crosslinking agent is 35 to 80 weight % of the total monomers, the crosslinking agent preferably being a diester and being present in an amount of at least 50 weight % of the total monomers, more preferably above 50 weight %, e.g., 55 to 80 weight % of the total monomers, i.e., (1) and (2) above plus any additional polymerizable monomers such as those exemplified hereinafter.

A part, e.g. 1 to 50% of the hydroxyalkyl or the hydroxyalkoxyalkyl 2-alkenoate can be replaced by another polymerizable monoethylenically unsaturated mohomer. This polymerizable monomer(s) should not be present in an amount to destroy the hydrophilic properties of the resulting gel. This, limited amounts of hydrophobic alkyl acrylate and alkyl methacrylates can be employed relative to hydrophilic acrylamide or methacrylamide, for example.

The novel self-supporting, shape-retaining gels containing upwards to 90% of FF retain their shape in water. When exposed to air for prolonged periods of time e.g., 30 days or more they exhibited excellent slow-release properties. They have utility as room fresheners and/or deodorizers, especially in miniature form, and as slow-releasing pellets for water systems.

By miniature form is meant consumer articles in the deodorizing and fragrancing areas used to mask odors in kitchens and bathrooms, such consumer articles being much smaller than typical household aerosol refresheners.

The novel articles release the various components (fractions) comprising the FF uniformly over an extremely long period of time thus giving a uniform, pleasant smell over the entire period. On the other hand, the prior art article during the early stages releases the "top notes" (the most volatile component) together with smaller disproportionate amounts of the higher boiling components. During the latter stages, the release of the higher boiling components dominates the FF released from the product. Thus, the FF released over the entire period is not uniform, a quality which is undesirable to the commercial trade.

Negligible shrinkage occurs with respect to the novel article over the FF extended slow-release period whereas substantial shrinkage (and eventual collapse) of the prior art product occurs in a much shorter period of time.

The novel product is self-supporting, relatively dry to the hand touch, and can be used without its being incorporated into a container. The prior art product gives a mushy, wet feel to the hand, and for these reasons it is containerized.

The novel gels, owing to the high active component loading, release this component continuously both in the air and in water for a long period of time, e.g., 6 months or more, and evidence nearly zero-order release properties. The active compound is preferably a fragrance, essence or a flavor, but a combination of these with a color, bactericidal agent, insect repellant, etc., can be prepared.

The possible use of gels prepared according to this invention is very broad. As solid air-fresheners they can be active for more than 40 days, e.g., 6 months, retain their shape and color, and produce the same amount of liberated fragrance as the conventional air-fresheners from much lower volume, which will enable a preparation of miniature solid air-fresheners. Inasmuch as the gels are self supporting, they do not require costly holders or containers and may be used for example as shaped objects (e.g., animal or flower shapes, appropriately colored), supplied in their own casting molds (made, for example, from polypropylene) which will be removed before use. Their small size and shape-retention makes them suitable to use as air fresheners in the filters of air-conditioning or heating units (pellets of the gels may be inserted into the filtering element), air-fresheners for cars or boats, air-fresheners and/or disinfecting pellets for vacuum cleaners to be inserted directly into the bags etc. Very suitable use includes sachets to be used in clothes closets or drawers, possibly containing a combination of a fragrance and an insect repellant.

As the fragrance release in air is expedited by heat, these gels are ideally suited to be used with candles or even electric lights, where the heat and air convention in the vicinity of the candle or electric bulb will cause a very strong release of fragrance.

In water, the release of the active ingredient is regulated and long lasting. The gel again holds its shape and does not disintegrate or swell. Strong release of fragrance was obtained in water of up to 30 days or longer. Therefore, these gels are suitable as toilet bowl deodorizers and disinfectants, or as fragrance suppliers for bath or showers. The latter use was tested by inserting a receptacle for the gel immediately before the show head. The fragrance release from the gel was sufficient to provide scented water when the shower was run for over two weeks. The mechanical properties of the gels may be improved, if need be, by incorporating fillers, e.g., as powders, or reinforcing fibers into their structure during polymerization.

The novel gel can be prepared by well known polymerization techniques using convention free radical initiators. The polymerization reaction can be carried out at over a wide temperature range, e.g., 20° to 105° C., frequently 35° to 40° C. to 90° C. A catalytically significant quantity of a free radical catalyst is employed, e.g., from 0.05 to 1 percent based on the total weight of polymerizable monomers. Typical catalysts include t-butyl peroctoate, isopropyl percarbonate, and benzoyl peroxide. Irradiation, e.g., by ultraviolet light or gamma rays, can also be employed to catalyze the polymerization reaction. There can also be used the catalysts in the aforementioned patents, for example.

The type and amount of the free-radical initiator used to effect the polymerization is not critical and will be obvious to those versed in the art. The only limitations imposed on the choice of the initiator is its solubility in the final (i.e., monomer(s) and active ingredients) mixture and its ability to initiate the polymerization at temperatures acceptable for the given active ingredient.

The polymerizable mixture can include, in addition to the 2-alkenoate ester and crosslinking agent discussed supra, at least one polymerizable monoethylenically unsaturated monomer such as an amine, amide, acid, ester, etc., including the alkylaminoalkyl acrylates and the methacrylates, vinyl and alkyl vinyl pyridines, the dialkylaminoalkyl alkyl vinyl ethers, the acrylamides and the methacrylamides, the pyrrolidones, the alkyl and cycloalkyl acrylates and the methacrylates, and others: aminoethyl methacrylate, monomethylaminoethyl methacrylate, t-butylaminoethyl methacrylate, p-amine styrene, dimethylaminoethyl acrylate, acrylate, piperidinoethyl methacrylace, morpholinoethyl, methacrylate, 2-vinylpyridine, 2-ethyl-5-vinylpyridine, dimethylaminopropyl methacrylate, dimethylaminoethyl vinyl sulfide, diethylaminoethyl vinyl ether, aminoethyl vinyl ether, N-vinyl-2-pyrrolidone, acrylamide, N-methacrylamide, N-phenylacrylamide, N,N-dimethylacrylamide, N,N-diarylacrylamide, N-methyl-N-phenylacrylamide, methacrylamide, N,N-dimethylmethacrylamide, N,N-diphenylmethacrylamide, N-hydroxyethyl-N-methylmethacrylamide, methyl methacrylate, butyl acrylate, cyclohexyl methacrylate, acrylic acid, methacrylic acid, fumaric acid, itaconic acid, citraconic acid, vinyl sulfonic acid.

Illustrative crosslinking agents include ethylene glycol diacrylate, ethylene glycol dimethacrylate, 1,2-butylene dimethacrylate, 1,3-butylene dimethacrylate, 1,4-butylene dimethacrylate, propylene glycol diacrylate, propylene glycol dimethacrylate, diethylene glycol dimethacrylate, dipropylene glycol dimethacrylate, divinylbenzene, divinyltoluene, divinyl tartrate, triallyl melamine, glycerine trimethacrylate, diallyl maleate, diallyl monoethylene glycol citrate, allyl vinyl maleate, diallyl itaconate, ethylene glycol diester of itaconic acid, divinylsulfone, triallyl phosphite, polyester of maleic anhydride with triethylene glycol, polyallyl glucose, pentaallyl sucrose, sucrose diacrylate, glucose dimethacrylate, divinyl citraconate, diallyl fumarate, glycidyl methacrylate, allyl methacrylate, and vinyl methacrylate. The crosslinking agent(s) usually, but not necessarily have at least two ethylenically unsaturated double bonds. The most suitable crosslinking agents are dimethacrylates and/or diacrylates of the ethylene glycol homologues, including mono- di-, tri- tetra-, poly-, etc. ethylene glycol. Various other bi and poly-functional ethylenically unsaturated monomers are also appropriate as indicated above.

Fillers can be for example pyrogenic silica, e.g., Aerosil 380, diatomaceous earth, Fullers earth, bentonite, alumina, wood flour, activated carbon and the like. Fibers natural or man-made are suitable fillers as well.

If for a given use it is not necessary to prepare gels with a very high loadings of the active ingredients(s), inert solvents may be used advantageously. For hydrogels which will be used in air, high-boiling solvents, compatible with the monomers and the active ingredients, with no or low odor and low vapor pressure are preferred. Illustrative of suitable solvents are ethylene glycol, propylene glycol, dipropylene glycol, glycerol, glycerol diacetate (diacetin), 1,2 propandiolcarbonate, pentaerythritol, etc. These solvents can be used up to 80 weight % of the total composition preferably between 10 and 80 weight %. The use of inert solvents may in some cases allow the preparation of a hydrophilic gel according to the invention with active ingredients which otherwise would inhibit polymerization if used in large amounts.

The "active" ingredient is a fragrance, essence or flavor, i.e., the FF ingredient. Typical examples of such materials includes lemon oil, strawberry, orange oil, anethole, citral, biacetyl, menthol, anise, amyl acetate, ethyl acetate, lavender oil, pine, blue spruce, apple, spearmint, peppermint, spice mint, peach, attar of roses, apple (International Flavors and Fragrances #58125), pine (IFF 4276-X), spearmint (IFF V 30549), lime (IFF 3117 W), spice-mint (Gentry #401283-00), carnation-peach (Gentry #401186-00), lemon-verbenna (Ungerer C-454), soap fragrance (Roue Bertrand DuPont D 723), melon (American Aromatics #12), (Felton International): floral bouquet #221, leather musk bouquet #323, cream bouquet #800, rose bouquet #593A, green apple bouquet #503, pine bouquet #740A, strawberry #863.

There can also be added bactericidal agents, e.g., benzalkonium chloride, disinfecting agents, insect repellants, e.g., N,N-diethyl-m-toluamide, and pyrethrum flowers, etc.

There can be added soluble or insoluble dyes and pigments, e.g., FD&C yellow #5, D&C Red #9 (Thomasset Colors) D&C mint green (Pylam Products Co.), mercadium red light GP (Hercules), C.P. medium yellow (Hercules), titanium dioxide (Unitane—American Cyanamide), carbon black (Konstamm).

Unless otherwise indicated, all parts and/or percentages throughout this application are by weight.

The composition can comprise, consist essentially of or consist of the materials set forth.

The terms "polymer" and "copolymer" are used interchangeably herein and designate polymeric products obtained by the polymerization of two or more polymerizable monomers and/or polymerizable polymers and/or mixtures thereof.

The term "fragrance" as used in this application and claims is used in a generic sense to include not only fragrances, but also perfume oils, essence, flavors, various cuts, distillates and fractions which give aromas and flavors, and the like.

DESCRIPTION OF THE PREFERRED EMBODIMENTS

EXAMPLE 1

One part of 2-hydroxyethyl methacrylate, one part of ethylene glycol dimethacrylate, 0.01 part of t-butyl peroctoate and 8 parts of strawberry fragrance (Felton International, #863) were intimately mixed together. The mixture was deaerated in vacuo and bubbled with an inert gas (nitrogen) for 3 minutes. Polymerization was conducted at 80° C. for three hours. The resulting polymerized gel was slightly yellow, opaque and brittle.

When left in air, this gel lost 37.5 weight % of the initially present fragrance in 40 days. At the end of this period, it still smelled strong and held its shape.

After 30 days in water, the gel turned white, but did not lose its shape. At the end of this period, it was still capable of scenting the water perceptibly.

EXAMPLE 2

One part of 2-hydroxyethyl methacrylate, one part of ethylene glycol dimethacrylate, 0.01 part of azobis isobutyronitrile, 2 parts of strawberry fragrance (Felton International #863) and 6 parts of propylene glycol were polymerized as in Example 1. The gel lost in 40 days in air 83 weight % of the fragrance originally present, but was still smelling strong.

EXAMPLE 3

Six parts of HEMA, six parts of n-acrylamide and eight parts of ethylene glycol dimethacrylate were intimately mixed with ten parts of a fragrance, 69 parts of a solvent, 0.5 part of benzoyl peroxide and 0.5 part of dimethyl-p-toluidine.

The resulting mixture polymerized at room temperature in about ten minutes to soft, opaque gel, which nevertheless was self-supporting and released the fragrance strongly for more than 30 days. Fragrance used were:

(a) Felton Strawberry
(b) American Aromatic Florae, Lemon or Soap clean
(c) Perry Bros. Pine
(d) Excel Blue Spruce Thus each of the fragrances (a), (b), (c) and (d) can be used with each of solvents (1), (2) and (3) in this example. For example there can be used 10 parts of Felton Strawberry and 69 parts of propylene glycol.

EXAMPLE 4

(Solution 1) 0.5 parts of benzoyl peroxide was dissolved in 35 parts HEMA and 25 parts of ethyleneglycol dimethacrylate.

(Solution 2) 0.5 part of p-tolyliminodiethanol was dissolved in 20 parts fragrance and 19 parts diacetin.

The fragrances used were the same as in Example 3. Depending on the fragrance used, the two solutions when mixed polymerized between five and eight minutes to a clear hard, glassy gel with a dry surface.

This gel releases the fragrance strongly at room temperature (20°–22° C.) and at normal humidity (35–50%) for more than six weeks. The nature of the fragrance is not changed during the release period.

EXAMPLE 5

(Solution 1) 0.5 part of benzoyl peroxide was dissolved in 25 parts HEMA and 45 parts of ethyleneglycol dimethacrylate.

(Solution 2) 0.5 part of p-tolyliminodiethanol was dissolved in 30 parts of a suitable fragrance (see Example 3).

Both solutions upon mixing polymerized at room temperature in about 4–5 minutes to a clear, very hard and brittle gel.

This gel was broken on a grinding machine to particles between 1 to 5 mm. A cloth bag filled with these particles was used as a sachet in a clothes closet. The trapped fragrance was released for over 6 months.

The solvent, if any, and filler, if any, should be non-toxic for most normal uses.

What is claimed is:

1. A solid, self-supporting, slow-release hydrogel composition consisting of a flavor or fragrance in an amount of 5 to 90% of the total composition weight entrapped in a hydrophilic copolymer of monomers consisting of either (a) at least one hydroxy lower alkyl 2-alkenoate, hydroxy lower alkoxy lower alkyl 2-alkenoate or hydroxy lower (polyalkoxy) lower alkyl 2-alkenoate or with (a') another monoethylenically unsaturated copolymerizable monomer in an amount up to 50% by weight of component (a), the copolymerizable material not being present in an amount sufficient to destroy the hydrophylic properties of the copolymer, and (b) at least one polyethylenically unsaturated crosslinking agent, the amount of (a) being not over 65% of the total weight of monomers and the amount of (b) being 35 to 80% of the total weight of monomers and (c) 0 to 80% of the total weight of the composition of a solvent.

2. A composition according to claim 1 containing 10 to 80% of the solvent.

3. A composition according to claim 2 wherein the crosslinking agent is present in an amount of at least 50% of the total weight of monomers.

4. A composition according to claim 3 wherein the crosslinking agent is present in an amount of at least 55% of the total weight of monomers.

5. A solid, self-supporting, slow-release hydrogel composition according to claim 1 consisting of a flavor or fragrance in an amount of 5 to 90% of the total composition weight entrapped in a hydrophilic copolymer of monomers consisting of (a) at least one hydroxy lower alkyl 2-alkenoate, hydroxy lower alkoxy lower alkyl 2-alkenoate or hydroxy lower (polyalkoxy) lower alkyl 2-alkenoate, (a') another monoethylenically unsaturated copolymerizable monomer in an amount not over 50% by weight of component (a) the copolymerizable material not being present in an amount sufficient to destroy the hydrophylic properties of the copolymer, and (b) at least one polyethylenically unsaturated crosslinking agent, the amount of (a) and (b) being not over 65% of the total weight of monomers and the amount of (b) being 35 to 80% of the total weight of monomers and (c) 0 to 80% of the total weight of the composition of a solvent.

6. A solid, self-supporting, slow-release hydrogel composition according to claim 1 consisting of a flavor or fragrance in an amount of 5 to 90% of the total composition weight entrapped in a hydrophilic copolymer of monomers consisting of (a) at least one hydroxy lower alkyl 2-alkenoate, hydroxy lower alkoxy lower alkyl 2-alkenoate or hydroxy lower (polyalkoxy) lower alkyl 2-alkenoate and (b) at least one polyethylenically unsaturated crosslinking agent, the amount of (a) being not over 65% of the total weight of monomers and the amount of (b) being 35 to 80% of the total weight of monomers and (c) to 80% of the total weight of the composition of a solvent.

* * * * *